US012622796B2

(12) United States Patent
Xiao et al.

(10) Patent No.: US 12,622,796 B2
(45) Date of Patent: May 12, 2026

(54) CONVEYOR AND LUMEN APPARATUS CONVEYING SYSTEM

(71) Applicant: LIFETECH SCIENTIFIC (SHENZHEN) CO., LTD., Shenzhen (CN)

(72) Inventors: Benhao Xiao, Shenzhen (CN); Junqiang Zhang, Shenzhen (CN)

(73) Assignee: Lifetech Scientific (Shenzhen) Co., Ltd., Shenzhen (CN)

( * ) Notice: Subject to any disclaimer, the term of this patent is extended or adjusted under 35 U.S.C. 154(b) by 1023 days.

(21) Appl. No.: 17/779,760

(22) PCT Filed: Dec. 16, 2020

(86) PCT No.: PCT/CN2020/136981
§ 371 (c)(1),
(2) Date: May 25, 2022

(87) PCT Pub. No.: WO2021/129493
PCT Pub. Date: Jul. 1, 2021

(65) Prior Publication Data
US 2022/0409411 A1     Dec. 29, 2022

(30) Foreign Application Priority Data
Dec. 27, 2019     (CN) ......................... 201922456689.X

(51) Int. Cl.
A61F 2/966          (2013.01)
A61F 2/95           (2013.01)
(52) U.S. Cl.
CPC ............ *A61F 2/966* (2013.01); *A61F 2/9517* (2020.05)
(58) Field of Classification Search
CPC ...... A61F 2/966; A61F 2/9517; A61F 2/2436; A61F 2/2427–2439; A61F 2/95–97; (Continued)

(56) References Cited

U.S. PATENT DOCUMENTS 6,022,341 A     2/2000  Lentz
9,480,589 B2   11/2016  Breyer et al.
(Continued)

FOREIGN PATENT DOCUMENTS

CN          2768675 Y     4/2006
CN        106913949 A     7/2017
(Continued)

OTHER PUBLICATIONS

International Search Report mailed Mar. 18, 2021, in corresponding to International Application No. PCT/CN2020/136981; 8 pages (with English Translation).
(Continued)

*Primary Examiner* — Sarah W Aleman
*Assistant Examiner* — Mikail A Mannan
(74) *Attorney, Agent, or Firm* — Maier & Maier, PLLC

(57)          ABSTRACT

A conveyor and a lumen apparatus delivery system. The conveyor includes a sheath core tube, a delivery sheath and an operating handle. The proximal end of the sheath core tube and the proximal end of the delivery sheath are both connected to the operating handle. The delivery sheath and the sheath core tube are both a hollow tube. The delivery sheath is sleeved on the sheath core tube in an axially slidable manner, and the delivery sheath and the sheath core tube cooperatively define a storable cavity. The delivery sheath includes a loading portion, a pushing portion and a connecting portion. The proximal end of the loading portion is connected to the distal end of the pushing portion; the proximal end of the pushing portion is connected to the distal end of the connecting portion, and the proximal end of the connecting portion is connected to the operating handle.

17 Claims, 5 Drawing Sheets

(58) Field of Classification Search
CPC ....... A61F 2/2466; A61M 25/10–1038; A61M
25/0023; A61M 25/0136
See application file for complete search history.

(56)                References Cited

U.S. PATENT DOCUMENTS

| | | | | |
|---|---|---|---|---|
| 2004/0143239 | A1* | 7/2004 | Zhou ................. | A61M 25/0053 604/524 |
| 2007/0043430 | A1 | 2/2007 | Stinson | |
| 2008/0082083 | A1* | 4/2008 | Forde ........................ | A61F 2/97 604/527 |
| 2011/0218613 | A1* | 9/2011 | Leopold ................... | A61F 2/95 623/1.2 |
| 2014/0330219 | A1* | 11/2014 | Quint ...................... | A61F 2/966 604/264 |
| 2015/0290437 | A1* | 10/2015 | Rudakov ............ | A61B 17/1214 623/1.12 |
| 2016/0089126 | A1* | 3/2016 | Guo .................. | A61M 25/0147 604/95.04 |
| 2017/0296367 | A1 | 10/2017 | Dorn et al. | |

FOREIGN PATENT DOCUMENTS

| | | |
|---|---|---|
| CN | 107280829 A | 10/2017 |
| CN | 107427379 A | 12/2017 |
| CN | 108236532 A | 7/2018 |
| CN | 207898755 U | 9/2018 |
| CN | 108992221 A | 12/2018 |
| CN | 211934438 U | 11/2020 |

OTHER PUBLICATIONS

Extended Search Report issued on Jan. 8, 2024, in corresponding European Application No. 20905409.7, 7 pages.
Examination Report issued on Nov. 14, 2022, in corresponding Indian Application No. 202217034185, 5 pages.

* cited by examiner

CONVEYOR AND LUMEN APPARATUS CONVEYING SYSTEM

TECHNICAL FIELD

The embodiments relate to the field of interventional apparatuses, in particular to a conveyor and a lumen apparatus conveying system.

BACKGROUND

This section provides background information related to the present disclosure, which is not necessarily the prior art.

For vascular diseases, an interventional therapy is mainly to convey a conveyor loaded with a vascular stent to a pre-designated position of a vascular lesion by means of human puncture, and then a sheath is withdrawn to release the stent. The stent covers the vascular lesion position to achieve the objective of treating vascular diseases. The interventional therapy that is used to treat the vascular diseases has the characteristics of low cost, short treatment period and less trauma to a human body, so it has gradually become the mainstream way to treat the vascular diseases.

The interventional therapy has certain requirements on a delivery sheath of the conveyor, which are reflected in the following aspects: (1) an inner diameter of the delivery sheath should be designed so that the stent can be loaded into the delivery sheath after being compressed. (2) The outer diameter of the deliver sheath should be designed so that, in an interventional clinical process, the delivery sheath loaded with the stent can successfully convey the stent to the pre-designated position of the lesion. (3) The delivery sheath has certain pushing performance and resistance to breaking to ensure that the stent can be successfully conveyed to the pre-designated position of the lesion without fracture or breakage. (4) The delivery sheath should have resistance to stretching to a certain extent. Since there is a certain release resistance in the stent releasing process, the resistance to stretching to a certain extent of the delivery sheath may avoid the risk that the stent fails in being released from the sheath after the sheath stretches under a relatively high pull force due to an extremely high release force of the stent. (5) The delivery sheath can or cannot be successfully withdrawn from the body after the stent has been released. It can be seen that whether the performance in all aspects of the delivery sheath is excellent or not plays an important role in the interventional treatment process using a vascular stent.

For the conveyor of a stent-like product with a larger radial size after compression, the requirements on the inner and outer diameter are higher. First, the inner diameter must be large enough to carry apparatuses such as compressed stents. In addition, in order to ensure that the conveyor enters the blood vessel successfully, when the inner diameter of the delivery sheath is kept unchanged, a smaller outer diameter of the delivery sheath is better, which will inevitably lead to a smaller wall thickness of the delivery sheath. However, for the delivery sheath with a smaller wall thickness, its pushing performance and resistance to breaking and stretching will be reduced, which may adversely affect the smooth operation of interventional surgery.

SUMMARY

Based on this, it is necessary to provide a conveyor. A conveying sheath or delivery sheath of the conveyor has a moderate inner diameter and outer diameter and has good pushing performance and good resistance to breaking and stretching.

A conveyor includes a sheath core tube, a delivery sheath and an operating handle. The proximal end of the sheath core tube and the proximal end of the delivery sheath are both connected to the operating handle. The delivery sheath and the sheath core tube are both a hollow tube. The delivery sheath is sleeved on the sheath core tube in an axially slidable manner, and the delivery sheath and the sheath core tube form a storable cavity. The delivery sheath includes a loading portion, a pushing portion and a connecting portion. The proximal end of the loading portion is connected to the distal end of the pushing portion; the proximal end of the pushing portion is connected to the distal end of the connecting portion, and the proximal end of the connecting portion is connected to the operating handle. The inner diameter of the loading portion is 0.05-1 mm larger than that of the pushing portion, and the outer diameter of the loading portion is equal to that of the pushing portion. The ratio of the axial length of the loading portion to the total length of the delivery sheath is in a range from 1% to 5%.

In one embodiment, the pushing portion includes a first region and a second region axially connected to the first region; the wall thickness of the second region is constant, and the inner diameter of the loading portion is 0.05 to 1 mm larger than that of the second region; the distal end of the first region is connected to the proximal end of the loading portion; and from the distal end to the proximal end of the first region, the wall thickness of the first region gradually increases from a numerical value equal to the wall thickness of the loading portion to a numerical value equal to the wall thickness of the second region.

In one embodiment, along the radial direction from inside to outside, the delivery sheath includes an inner tube, a middle tube, and an outer tube in sequence; the middle tube is sleeved on the inner tube; and the outer tube is sleeved on the middle tube.

In one embodiment, the inner tube is a polytetrafluoroethylene (PTFE) tube; the middle tube is a stainless steel wire woven net tube; and the outer tube is a Pebax tube.

In one embodiment, the distal end surface of the inner tube is flush with the distal end surface of the outer tube; and the distal end surface of the middle tube is closer to the proximal end surface of the inner tube than the distal end surface of the inner tube.

In one embodiment, the sheath core tube includes a first inner tube and a second inner tube fixedly connected to the proximal end of the first inner tube; and the outer diameter of the second inner tube is greater than that of the first inner tube.

In one embodiment, the conveyor further includes a sheath tube connector; the sheath tube connector is connected to the connecting portion of the delivery sheath; and the delivery sheath is connected to the operating handle through the sheath tube connector.

In one embodiment, the sheath tube connector includes a connecting part and a fixed part connected to the connecting part; the connecting part is sleeved on the connecting portion; the outer diameter of the connecting portion is greater than that of the pushing portion; and the fixed part is fixedly connected to the operating handle.

In one embodiment, the operating handle includes a fixed handle and a movable handle; the proximal ends of the sheath core tube and the delivery sheath are both axially threaded into the fixed handle and the movable handle; and the sheath core tube is fixedly connected to the fixed handle; and the delivery sheath is fixedly connected to the movable handle through the sheath tube connector.

A lumen apparatus conveying system includes a lumen apparatus and the above-mentioned conveyor. The lumen apparatus is accommodated in the storable cavity.

The inner diameter of the loading portion of the delivery sheath of the above-mentioned conveyor is 0.05 to 1 mm larger than that of the pushing portion, and the outer diameter of the loading portion is equal to that of the pushing portion. That is, when the outer diameter of the delivery sheath is not increased, the inner diameter of the loading portion is reasonably increased to make the inner diameter and the outer diameter moderate, so that carrying and conveying of the lumen apparatus may be successfully achieved. Furthermore, the ratio of the axial length of the loading portion to the total length of the conveying/delivery sheath is in a range from 1% to 5%, which avoids the influence of an extremely large axial length of the loading portion with the smaller wall thickness on the pushing performance and the resistance to breaking and stretching of the delivery sheath.

DETAILED DESCRIPTION OF THE EMBODIMENTS

In order to make the above objectives, features and advantages more obvious and understandable, the embodiments are described in detail below in conjunction with the accompanying drawings. Many specific details are described in the following descriptions to facilitate full understanding of the embodiments. However, the embodiments may be implemented in many different forms from those herein set forth, and those skilled in the art may make similar improvements without departing from the scope of the embodiments. Therefore, the embodiments are not limited by the specific embodiments described below.

Unless otherwise defined, all technical and scientific terms used herein have the same meaning as commonly understood by those of ordinary skill in the art to which the present disclosure belongs. The terms used are for the purpose of describing specific embodiments only and are not are intended as limiting.

In the field of interventional medical apparatuses, "distal end" is defined as the end far from the operator during surgery, and "proximal end" is defined as the end close to the operator during surgery. "Axial" refers to the direction parallel to the connecting line between the center of a distal end of the medical apparatus and the center of a proximal end of the medical apparatus, and "radial" refers to the direction perpendicular to the above axial direction.

4

Figure 1:
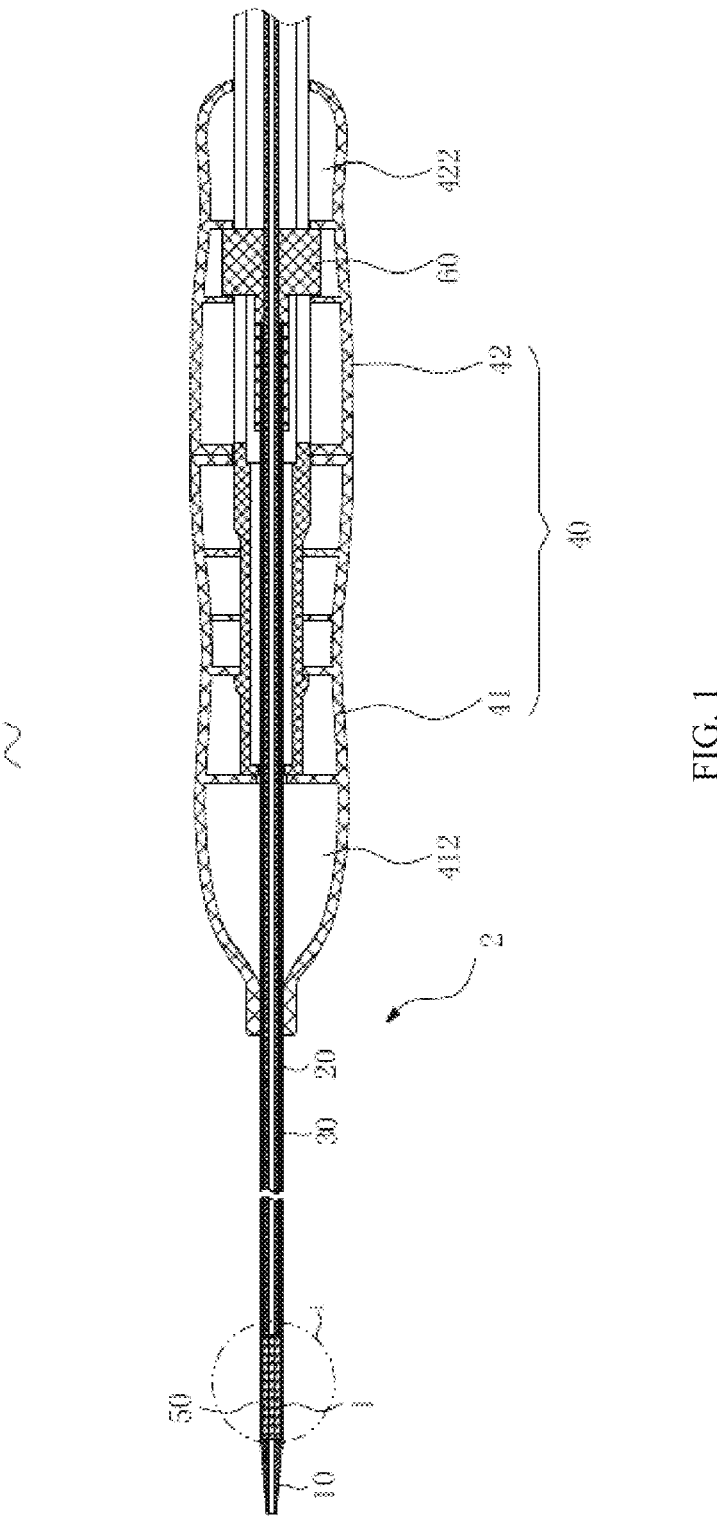
FIG. 1 is a schematic structural diagram of a lumen apparatus conveying system of one embodiment.

Referring to FIG. 1, a lumen apparatus conveying system 100 of one embodiment includes a lumen apparatus 1 and a conveyor 2.

In one embodiment, the lumen apparatus 1 is a vascular stent. In one embodiment, the lumen apparatus 1 is a stent-graft that includes a supporting skeleton and a cover membrane covering the supporting skeleton. The cover membrane is covered on the supporting skeleton to form a circumferentially closed lumen structure. In one embodiment, the lumen apparatus 1 is a bare stent, namely it only includes the supporting skeleton and does not include the cover membrane.

Figure 2:
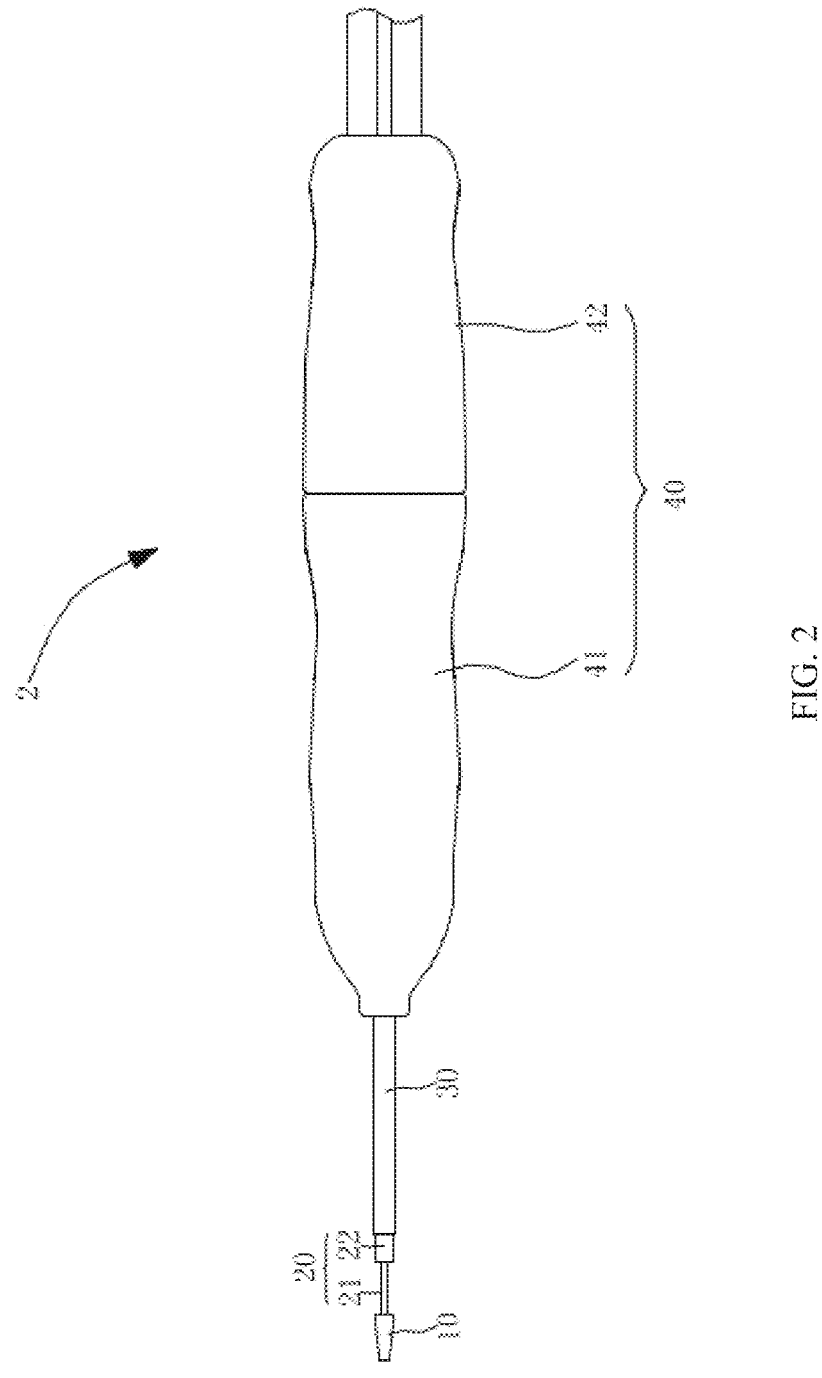
FIG. 2 is a schematic structural diagram of a conveyor of one embodiment.
Figure 3:
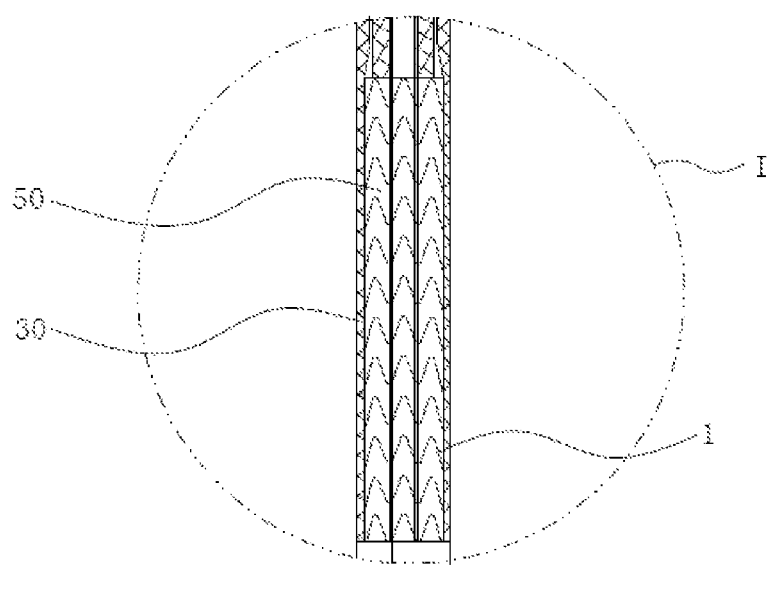
FIG. 3 is a partially enlarged diagram of FIG. 1.

Referring to FIG. 1 and FIG. 2 together, the conveyor 2 includes a sheath core tube 20, a delivery sheath 30, and an operating handle 40. The sheath core tube 20 and the delivery sheath 30 are both a hollow tube. The delivery sheath 30 is sleeved on the sheath core tube 20 and is coaxial with the sheath core tube 20. Furthermore, the delivery sheath 30 is axially slidable relative to the sheath core tube 20. The delivery sheath 30 and the sheath core tube 20 are encircled to form a ring-shaped storable cavity 50. The lumen apparatus 1 after compression is accommodated in the ring-shaped storable cavity 50, as shown in FIG. 3.

In one embodiment, referring to FIG. 2 again, the sheath core tube 20 includes a first inner tube 21 and a second inner tube 22 fixedly connected to the proximal end of the first inner tube 21. The first inner tube 21 and the second inner tube 22 are both a hollow tubular member. The first inner tube 21 is of a tubular structure with an equal outer diameter, and the second inner tube 22 is also of a tubular structure with an equal outer diameter. The outer diameter of the first inner tube 21 is less than that of the second inner tube 22. In one embodiment, the inner diameter of the first inner tube 21 is equal to the inner diameter of the second inner tube 22. In this embodiment, the sheath core tube 20 may be formed as an integral tube. In other embodiments, the inner diameter of the first inner tube 21 is less than that of the second inner tube 22, and the second inner tube 22 is sleeved and fixed at the proximal end of the first inner tube 21. The distal end of the second inner tube 22 may be connected to the proximal end of the first inner tube 21 in an adhered manner, welded manner, or other manners.

The sheath core tube 20 includes the inner tube 22 with a larger outer diameter, so that the second inner tube 22 may well support the delivery sheath 30 in a region of the delivery sheath 30 not covering the lumen apparatus 1, which is conducive to preventing or avoiding the delivery sheath 30 from bending.

Figure 4:
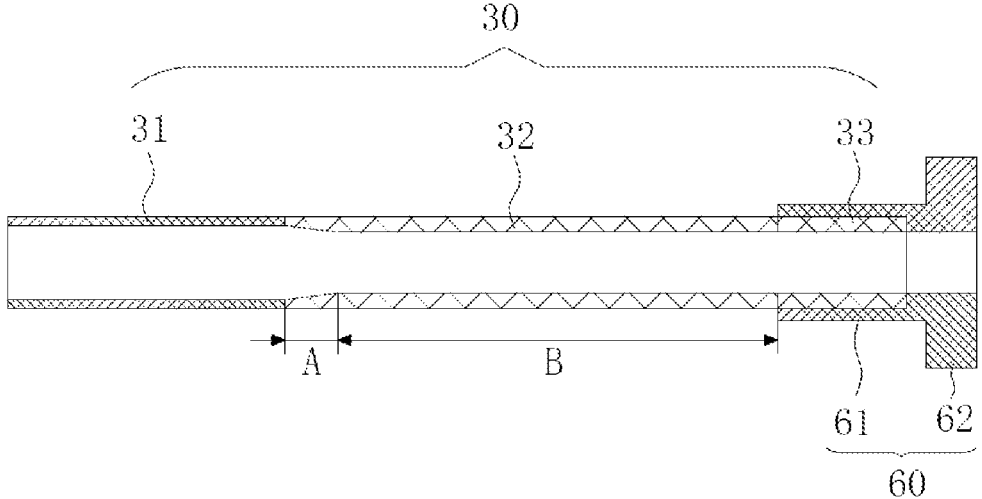
FIG. 4 is a schematic state diagram illustrating that a delivery sheath and a sheath tube connector are connected of one embodiment.

Referring to FIG. 4, the delivery sheath 30 includes a loading portion 31, a pushing portion 32, and a connecting portion 33 which are axially connected in sequence. The proximal end of the loading portion 31 is connected to the distal end of the pushing portion 32; the proximal end of the pushing portion 32 is connected to the distal end of the connecting portion 33; and the proximal end of the connecting portion 33 is connected to the operating handle 40 (not shown in FIG. 4).

The loading portion 31 is a hollow tube with a constant inner diameter and outer diameter. The inner diameter of the loading portion 31 is 0.05 to 1 mm larger than that of the pushing portion 32, and the outer diameters of the loading portion 31 is equal to that of the pushing portion 32. The ratio of the axial length of the loading portion 31 to the total length of the delivery sheath 30 is in a range from 1% to 5%. The axial length of the loading portion 31 with a smaller wall thickness only accounts for 1% to 5% of the total length of the delivery sheath 30, which is conductive to preventing or avoiding the delivery sheath 30 from being fractured or broken in a conveying process. Furthermore, the consequence in the releasing process that the lumen apparatus 1 fails in being released after the delivery sheath 30 stretches under a relatively high pull force due to an extremely high release force of the lumen apparatus 1 is avoided.

In one embodiment, the pushing portion 32 is a hollow tube with a constant inner diameter and outer diameter.

In another embodiment, referring to FIG. 4, the pushing portion 32 includes a first region A and a second region B axially connected to the first region A. The distal end of the first region A is connected to the proximal end of the loading portion 31, and the proximal end of the first region A is connected to the distal end of the second region B. The wall thickness of the second region B is constant, and the inner diameter of the loading portion 31 is 0.05 to 1 mm larger than that of the second region B. When the first region A axially extends from the distal end to the proximal end, the wall thickness of this region gradually increases from a numerical value equal to the wall thickness of the loading portion 31 to a numerical value equal to the wall thickness of the second region B. The axial length of the first region A is extremely small, which is about 3 to 10 mm, so that it will not affect the overall pushing performance and the overall resistance to breaking and stretching of the pushing portion 32.

Figure 5:
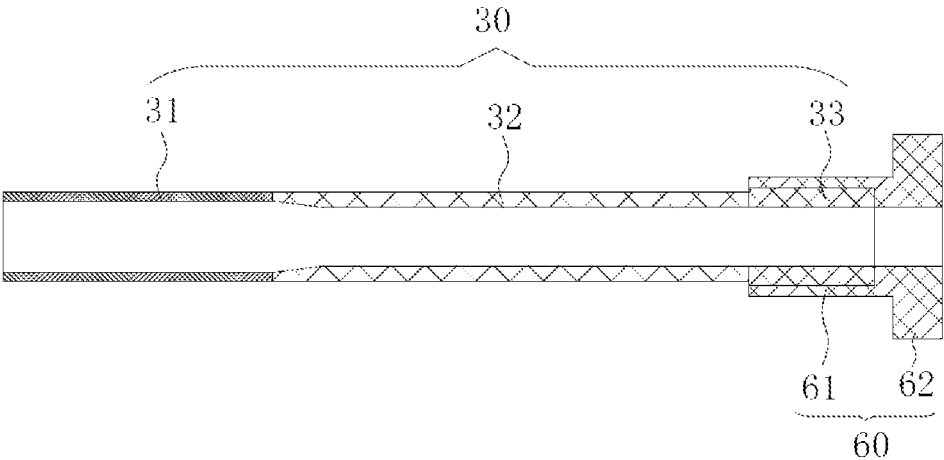
FIG. 5 is a schematic state diagram illustrating that a delivery sheath and a sheath tube connector are connected of another embodiment.

The inner diameter of the connecting portion 33 is equal to that of the pushing portion 32. The outer diameter of the connecting portion 33 is equal to that of the pushing portion 32 (as shown in FIG. 4) or the outer diameter of the connecting portion 33 is larger than that of the pushing portion 32 (as shown in FIG. 5). The outer diameter of the connecting portion 33 is equal to that of the pushing portion 32 so that the machining is more convenient. The delivery sheath 30 may be of an integrated structure, namely the delivery sheath 30 including the loading portion 31, the pushing portion 32, and the connecting portion 33 is injection-molded. Or, the loading portion 31, the pushing portion 32, and the connecting portion 33 are axially connected in sequence to form the delivery sheath 30.

The pushing portion 32 includes a first region A with a gradually changing wall thickness so that the wall thickness of the loading portion 31 is smoothly transitioned to the wall thickness of the pushing portion 32. In this design, on the one hand, the machining is more convenient; and on the other hand, dramatic changes in stress may be avoided, so that the breaking risk in the process that the delivery sheath 30 enters a complex blood vessel due to concentrated stress easily caused at a bent position may be avoided.

Figure 6:
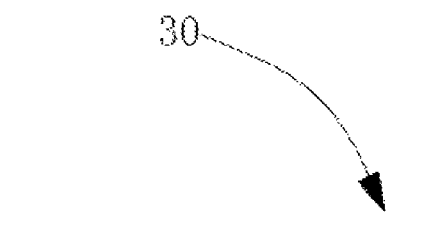
FIG. 6 is a schematic diagram of a partially sectional structure of a loading portion of a delivery sheath of one embodiment.
Figure 6:
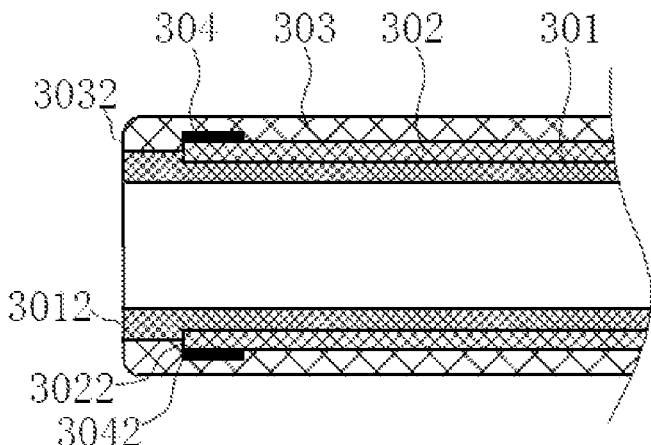

Referring to FIG. 6, along the radial direction from inside to outside (from an inner chamber to an outer wall), the delivery sheath 30 includes an inner tube 301, a middle tube 302, and an outer tube 303 in sequence. The middle tube 302 is sleeved on the inner tube 301, and the outer tube 303 is sleeved on the middle tube 302. Furthermore, the inner tube 301, the middle tube 302, and the outer tube 303 are closely fitted to one another to form a compact sheath wall. For example, the inner tube 301, the middle tube 302, and the outer tube 303 are melted into a whole in a hot melting manner after they are disposed according to the above method.

In one embodiment, the inner tube 301 is a polytetrafluoroethylene (PTFE) tube; the middle tube 302 is a stainless steel wire woven net tube; and the outer tube 303 is a Pebax tube. The inner tube 301, the middle tube 302, and the outer tube 303 are respectively made of the three materials, and it is reasonably set that the ratio of the axial length of the loading portion 31 to the total length of the delivery sheath 30 is in a range from 1% to 5%. On the one hand, the whole delivery sheath 30 has enough structural strength and has enough pushing performance and resistance to breaking and stretching, so as to ensure smooth conveying and releasing and increase the success rate of operation. Meanwhile, the phenomenon that it is hard for the delivery sheath 30 to pass through a bent vascular part due to extremely high structural strength after the inner tube 301, the middle tube 302, and the outer tube 303 are integrated may also be avoided.

Referring to FIG. 6, the distal end surface 3012 of the inner tube 301 is flush with the distal end surface 3032 of the outer tube 303; and the distal end surface 3022 of the middle tube 302 is closer to the proximal end surface of the inner tube 301 than the distal end surface 3012 of the inner tube 301 (the proximal end surface of the inner tube 301 is not shown in FIG. 6). The proximal end surface of the inner tube 301, the proximal end surface of the outer tube 303, and the proximal end surface of the middle tube 302 are flush.

Further, referring to FIG. 1 and FIG. 2 again, the conveyor 2 further includes a guide head 10. The guide head 10 is of a conical hollow cavity structure with openings in two ends. The guide head 10 can be a TIP guide head so that the guide head 10 has good flexibility. The distal end of the sheath core tube 20 extends into the guide head 10 from the open end of the proximal end of the guide head 10 and is fixedly connected to the guide head 10. The cavity of the sheath core tube 20 is communicated with the cavity of the guide head 10 to form a guide wire channel, so as to ensure that the conveyor 2 loaded with the lumen apparatus 1 successfully enter a blood vessel under the guidance of the guide wire. For example, the first inner tube 21 of the sheath core tube 20 is fixedly connected to the guide head 10.

In order to ensure the stability of loading, in one embodiment, in a loaded state, part of the distal end of the delivery sheath 30 is sleeved on the guide head 10; the distal end surface 3022 of the middle tube 302 is closer to the proximal end surface of the inner tube 301 than the distal end surface 3012 of the inner tube 301, so that the distal end of the delivery sheath 30 is softer. When the distal end of the delivery sheath 30 is sleeved on the guide head 10, the rigidity of the guide head 10 is not significantly increased, and the guide head 10 successfully passes through a bent vascular path.

In one embodiment, the distance between the distal end surface 3012 of the inner tube 301 and the distal end surface 3022 of the middle tube 302 is 1 to 3 mm.

In one embodiment, as shown in FIG. 6, the conveying/delivery sheath 30 further includes a mark ring 304. The mark ring 304 is sleeved on the distal end of the middle tube 304. Furthermore, the mark ring 304 is embedded into the wall of the outer tube 303. The material of the mark ring 304 is a material with good visuality under digital subtraction angiography (DSA) and other medical image equipment. Disposing the mark ring 304 is favorable for improving the visuality of the delivery sheath 30. In one embodiment, the distal end surface 3042 of the mark ring 304 is flush with the distal end surface 3022 of the middle tube 302. The distal end surface 3042 of the mark ring 304 is flush with the distal end surface 3022 of the middle tube 302, so that the mark ring 304 is provided to improve the visuality, but not increase the rigidity of the distal end of the delivery sheath 30. When the delivery sheath 30 is sleeved on the guide head 10, the rigidity of the guide head 10 is not significantly increased.

Referring to FIG. 1 and FIG. 2 again, the operating handle 40 includes a fixed handle 41 and a movable handle 42. The fixed handle 41 has a first holding cavity 412 with openings in two ends, and the openings in two ends are axially opposite. The movable handle 42 has a second holding cavity 422 with openings in two ends, and the openings in the two ends are axially opposite.

The proximal ends of the sheath core tube 20 and the delivery sheath 30 are both axially threaded into the fixed handle 41 and the movable handle 42. The sheath core tube 20 is fixedly connected to the fixed handle 41. The delivery sheath 30 is fixedly connected to the movable handle 42. The movable handle 42 is axially slidable relative to the fixed handle 41 and drives the delivery sheath 30 to correspondingly axially slide. The movable handle 42 drives the delivery sheath 30 to axially slide away from the fixed handle 41 to release the lumen apparatus 1.

Referring to FIG. 1, in one embodiment, the delivery sheath 30 is connected to the operating handle 40 through a sheath tube connector 60. Specifically, the delivery sheath 30 is fixedly connected to the movable handle 42 through the sheath tube connector 60. As shown in FIG. 4 and FIG. 5, the sheath tube connector 60 includes a connecting part 61 and a fixed part 62 connected to the connecting part 61. The connecting part 61 has an inner chamber. The connecting part 61 is sleeved on the connecting portion 33 of the delivery sheath 30. The fixed part 62 is connected to the inner wall of the movable handle 42 to achieve fixed connection between the delivery sheath 30 and the movable handle 42. It should be noted that connecting the fixed part 62 to the inner wall of the movable handle 42 refers to direct connection or indirect connection. For example, a clamping plate fixed on the inner wall of the movable handle 42 may be provided. And the fixed part 62 is fixedly connected to the clamping plate.

In one more specific embodiment, the connecting part 61 is of a hollow cylindrical structure, and the fixed part 62 is of two sheet-like structures. The two sheet-like structures are symmetrically arranged on a side surface of the connecting part 61 by taking a central axis of the connecting part 61 as a symmetry axis and extend from the side surface of the connecting part 61 towards a direction away from the side surface.

The connecting part 61 is sleeved on the connecting portion 33 of the delivery sheath 30 and is fixedly connected to the connecting portion 33. The fixed connection includes, but is not limited to, gluing, ultrasonic welding, threaded connection, injection connection, and other known connection ways. The outer diameter of the connecting portion 33 is greater than that of the pushing portion 32, so that the connecting part 61 of the sheath tube connector 60 and the connecting portion 33 may be fully combined, which may increase the fixed connection degree between them, which enhances a connection force between the sheath tube connector 60 and the delivery sheath 30 and avoids the risk that the delivery sheath 30 is separated from the sheath tube connector 60 under extremely high release resistance.

When the above-mentioned lumen apparatus conveying system 100 is assembled, the lumen apparatus 1 after compression is put into the storable cavity 50 formed by encircling the sheath core tube 20 and the delivery sheath 30, so as to load the lumen apparatus 1 into the conveyor 2. In the loaded state, the distal end surface of the delivery sheath 30 abuts against the proximal end surface of the guide head 10 or the distal end of the delivery sheath 30 is sleeved on the proximal end of the guide head 10. At this time, the lumen apparatus 1 (as shown in FIG. 1) is constrained by the delivery sheath 30.

In a surgical procedure, after the lumen apparatus 1 is conveyed to a lesion part, the movable handle 42 axially slides to the proximal end to drive the delivery sheath 30 to axially slide towards the proximal end, so as to release the lumen apparatus 1.

The inner diameter of the loading portion 31 of the delivery sheath 30 of the above-mentioned conveyor 2 is 0.05 to 1 mm larger than that of the pushing portion 32, and the outer diameter of the loading portion 31 is equal to that of the pushing portion 32. That is, when the outer diameter of the delivery sheath 30 is not increased, the inner diameter of the loading portion 31 is reasonably increased to make the inner diameter and the outer diameter moderate, so that carrying and conveying of the apparatus may be successfully achieved. Furthermore, the ratio of the axial length of the loading portion 31 to the total length of the delivery sheath 30 is in a range from 1% to 5%, which avoids the influence of an extremely large axial length of the loading portion 31 with the smaller wall thickness on the pushing performance and the resistance to breaking and stretching of the conveying/delivery sheath 30.

The above-mentioned conveyor 2 may be applicable to the lumen apparatus 1 having a larger radial size after compression and is more applicable to the lumen apparatus 1 having a larger radial size after compression, so that the adaptability is good.

Therefore, the lumen apparatus conveying system 100 is used to treat vascular diseases, which is favorable for successfully carrying out an implanting operation and avoiding a secondary trauma to a patient caused by a surgery failure.

The various features of the above-mentioned embodiments may be combined in any manner. In order to make the description concise, all possible combinations of various features in the above-described embodiments are not described. However, as long as the combinations of these features do not have contradictions, they shall fall within the scope of the embodiments.

The above-mentioned embodiments only describe several embodiments, and their descriptions are more specific and detailed, but they are understood as non-limiting. It should be noted that those of ordinary skill in the art may further make various modifications, alterations, and/or transformations without departing from the scope of the embodiments, and these modifications, alterations, transformations and improvements all fall within the scope of the present embodiments.

The invention claimed is:

1. A conveyor, comprising: a sheath core tube, a delivery sheath and an operating handle, wherein a proximal end of the sheath core tube and a proximal end of the delivery sheath are both connected to the operating handle; each of the delivery sheath and the sheath core tube is a hollow tube; the delivery sheath is sleeved on the sheath core tube in an axially slidable manner, and the delivery sheath and the sheath core tube cooperatively define a storable cavity; the delivery sheath is an integrated structure, the delivery sheath comprises a loading portion, a pushing portion, and a connecting portion, and the loading portion, pushing portion, and connecting portion are integrally formed; a proximal end of the loading portion is connected to a distal end of the pushing portion; a proximal end of the pushing portion is connected to a distal end of the connecting portion, and a proximal end of the connecting portion is connected to the operating handle; an inner diameter of the loading portion is 0.05-1 mm larger than that of the pushing portion, and an outer diameter of the loading portion is equal to that of the pushing portion; and a ratio of an axial length of the loading portion to a total length of the conveying/delivery sheath is in a range from 1% to 5%;

wherein the operating handle comprises a fixed handle and a movable handle, the fixed handle is positioned distally of the movable handle, and a proximal end of the fixed handle is opposite to a distal end of the movable handle;

the proximal ends of the sheath core tube and the delivery sheath are both axially threaded into the fixed handle and the movable handle; and the sheath ore tube is fixedly connected to the fixed handle, and the delivery sheath is fixedly connected to the movable handle, such that the movable handle is configured to drive the delivery sheath to slide axially relative to the sheath core tube to release a lumen apparatus.

2. The conveyor according to claim 1, wherein the pushing portion comprises a first region and a second region axially connected to the first region; a wall thickness of the second region is constant, and an inner diameter of the loading portion is 0.05 to 1 mm larger than that of the second region; a distal end of the first region is connected to the proximal end of the loading portion; and from the distal end to a proximal end of the first region, a wall thickness of the first region gradually increases from a numerical value equal to a wall thickness of the loading portion to a numerical value equal to the wall thickness of the second region.

3. The conveyor according to claim 1, wherein along a radial direction from inside to outside, the delivery sheath comprises an inner tube, a middle tube, and an outer tube in sequence; the middle tube is sleeved on the inner tube; and the outer tube is sleeved on the middle tube.

4. The conveyor according to claim 3, wherein the inner tube is a polytetrafluoroethylene (PTFE) tube; the middle tube is a stainless steel wire woven net tube; and the outer tube is a Pebax tube.

5. The conveyor according to claim 3, wherein a distal end surface of the inner tube is flush with a distal end surface of the outer tube; and a distal end surface of the middle tube is closer to a proximal end surface of the inner tube than the distal end surface of the inner tube.

6. The conveyor according to claim 1, wherein the conveyor further includes a guide head, which is a conical hollow cavity structure with openings in two ends, the sheath core tube comprises a first inner tube and a second inner tube fixedly connected to a proximal end of the first inner tube; and an outer diameter of the second inner tube is greater than that of the first inner tube; a distal end of the sheath core tube extends into the guide head from the open end of a proximal end of the guide head and is fixedly connected to the guide head, a cavity of the sheath core tube is communicated with the cavity of the guide head to form a guide wire channel.

7. The conveyor according to claim 1, wherein the conveyor further comprises a sheath tube connector; the sheath tube connector is connected to the connecting portion of the delivery sheath; and the delivery sheath is connected to the operating handle through the sheath tube connector.

8. The conveyor according to claim 7, wherein the sheath tube connector comprises a connecting part and a fixed part connected to the connecting part; the connecting part is sleeved on the connecting portion; an outer diameter of the connecting portion is greater than that of the pushing portion; and the fixed part is fixedly connected to the operating handle.

9. The conveyor according to claim 7, wherein the delivery sheath is fixedly connected to the movable handle through the sheath tube connector.

10. A lumen apparatus conveying system, comprising: a lumen apparatus and the conveyor according to claim 1, and the lumen apparatus is accommodated in a storable cavity.

11. The conveyor according to claim 2, wherein an axial length of the first region is 3 to 10 mm.

12. The conveyor according to claim 5, wherein a distance between the distal end surface of the inner tube and the distal end surface of the middle tube is 1 to 3 mm.

13. The conveyor according to claim 5, wherein the delivery sheath further includes a mark ring, which is sleeved on the distal end of the middle tube and embedded into a wall of the outer tube, and a distal end surface of the mark ring is flush with the distal end surface of the middle tube.

14. The conveyor according to claim 6, wherein the first inner tube is a tubular structure with an equal outer diameter, and the second inner tube is also a tubular structure with an equal outer diameter; an inner diameter of the first inner tube is less than that of the second inner tube, and the second inner tube is sleeved and fixed at the proximal end of the first inner tube.

15. The conveyor according to claim 6, wherein an inner diameter of the first inner tube is equal to an inner diameter of the second inner tube, and the sheath core tube is formed as an integral tube.

16. The conveyor according to claim 6, wherein in a loaded state, a distal end surface of the delivery sheath abuts against a proximal end surface of the guide head, or a distal end of the delivery sheath is sleeved on the proximal end of the guide head.

17. The conveyor according to claim 8, wherein the connecting part is a hollow cylindrical structure, the fixing part is two sheet-like structures, and the two sheet-like structures are symmetrically arranged on a side surface of the connecting part by taking a central axis of the connecting part as a symmetry axis and extend from the side surface of the connecting part towards a direction away from the side surface.

* * * * *